United States Patent [19]

O'Neill et al.

[11] Patent Number: 5,278,342
[45] Date of Patent: Jan. 11, 1994

[54] VAPOR PHASE CHLORINATION OF DIFLUOROMETHYL METHYL ETHER

[75] Inventors: Gerald J. O'Neill, Arlington, Mass.; Robert J. Bulka, Merrimack, N.H.

[73] Assignee: Hampshire Chemical Corp., Lexington, Mass.

[21] Appl. No.: 25,009

[22] Filed: Mar. 15, 1993

Related U.S. Application Data

[63] Continuation-in-part of Ser. No. 858,387, Mar. 25, 1992, Pat. No. 5,196,600.

[51] Int. Cl.$^5$ ............................................. C07C 41/22
[52] U.S. Cl. .................................. 568/684; 568/683; 204/157.92
[58] Field of Search ............................... 568/684, 683; 204/157.92

[56] References Cited

U.S. PATENT DOCUMENTS

| | | |
|---|---|---|
| 2,066,905 | 1/1937 | Booth . |
| 2,533,132 | 12/1950 | McBee . |
| 3,461,213 | 8/1969 | Terrell ............................. 568/684 |
| 3,663,715 | 5/1972 | Terrell ............................. 568/684 |
| 3,689,459 | 9/1972 | Reagan . |
| 3,806,602 | 4/1974 | Croix ............................... 424/342 |
| 3,879,474 | 4/1975 | Croix . |
| 3,887,439 | 6/1975 | Hutchinson ....................... 203/63 |
| 3,897,502 | 7/1975 | Russell et al. . |
| 4,025,567 | 5/1977 | Hutchinson et al. . |
| 4,041,148 | 8/1977 | Simons et al. ................... 424/45 |
| 4,113,435 | 9/1978 | Lagow et al. .................. 422/191 |
| 4,139,607 | 2/1979 | Simons et al. ................... 424/45 |
| 4,149,018 | 4/1979 | Bell et al. ....................... 568/684 |
| 4,504,686 | 0/1985 | Takamatsu ..................... 568/684 |
| 4,874,901 | 10/1989 | Halpern et al. ................ 568/683 |
| 4,961,321 | 10/1990 | O'Neill et al. .................. 62/114 |
| 5,026,924 | 6/1991 | Cicco ............................... 568/683 |
| 5,185,474 | 2/1993 | O'Neill ............................. 568/684 |
| 5,196,600 | 3/1993 | O'Neill ............................. 568/684 |

FOREIGN PATENT DOCUMENTS

| | | |
|---|---|---|
| 949978 | 6/1974 | Canada . |
| 0352034 | 1/1990 | European Pat. Off. . |
| 0450855 | 10/1991 | European Pat. Off. . |
| 0518506 | 12/1992 | European Pat. Off. . |
| 2248617 | 4/1992 | United Kingdom . |

OTHER PUBLICATIONS

Chemical Abstract, vol. 52, 44676 (1958); "Methylene Derivatives as Intermediates in Polar Reactions", Journal of the American Chem. Society, 79, 5493-6 (1957).
Chemical Abstract, vol. 55, 12270 (1961).
Chemical Abstract, vol. 55 23312 (b) (1961).
Chemical Abstract, vol. 55, 27012 (i) (1961).
Chemical Abstract, vol. 56, 9938 (c) (1962).
Chemical Abstract, vol. 82, 43287 (j) (1975).
Chemical Abstract, vol. 73, 14080 (1970).
Chemical Abstract, vol. 58, 23556 (g) (1964).
Chemical Abstract, vol. 53, 27013 (a) (1961).

Primary Examiner—Howard T. Mars
Attorney, Agent, or Firm—Nields & Lemack

[57] ABSTRACT

The synthesis of fluorinated dimethyl ethers of the formula $CF_2HOCCl_xF_yH_{3-(x+y)}$ wherein x is 0, 1 or 2; y is 1, 2 or 3; and wherein (x+y) is 1, 2 or 3. The process involves chlorination of methyl difluoromethyl ether in the presence of oxygen to form a chlorinated reaction product of the formula $CF_2HOCH_{3-z}Cl_z$ wherein z is 1 or 2, and wherein the formation of $CF_2HOCCl_3$ is inhibited. The resulting compound(s) is then fluorinated with HF before or after separation, to give a fluorinated reaction product including the aforementioned fluorinated dimethyl ethers.

11 Claims, No Drawings

VAPOR PHASE CHLORINATION OF DIFLUOROMETHYL METHYL ETHER

This application is a continuation-in-part of Ser. No. 858,387 filed Mar. 25, 1992, now U.S. Pat. No. 5,196,600.

BACKGROUND OF THE INVENTION

This invention relates in general to fluorinated dimethyl ethers and specifically to methyl difluoromethyl ether as a starting material for the synthesis of fluorinated dimethyl ethers. Such fluorinated dimethyl ethers, including bis(difluoromethyl)ether ($CHF_2OCHF_2$), have utility has CFC alternatives, particularly for use as refrigerants, blowing agents, etc.

Bis(difluoromethyl)ether has been prepared previously by chlorination of dimethyl ether followed by isolation and fluorination of bis(dichloromethyl)ether. The chlorination step resulted in a complex mixture of chlorinated dimethyl ethers, some of which were unstable, e.g. to distillation, from which bis(dichloromethyl)ether was separated. Moreover, chloromethyl methyl ether and bis(chloromethyl)ether are produced by this reaction, and are carcinogens.

Another approach to the synthesis of methyl difluoromethyl ether is disclosed by Hine and Porter in Methylene derivatives as intermediates in polar reaction VIII. Difluoromethylene in the Reaction of Chlorodifluoromethane with Sodium Methoxide, published in the Journal of the American Chemical Society 79, 5493-6 (1957). This article describes a reaction mechanism wherein the desired difluoromethyl-methyl-ether is synthesized in a batch reaction in a fixed ratio with the by-product trimethyl-orthoformate, while continuously refluxing the unreacted feed. However, not only does this reaction produce large amounts of trimethylorthoformate, but also the product itself breaks down to trimethylorthoformate, resulting in less than advantageous yields of the desired difluoromethyl methyl ether.

U.S. Pat. No. 5,185,474, the disclosure of which is hereby incorporated by reference, discloses avoiding the production of such carcinogens and unstable compounds by using methyl difluoromethyl ether as a starting material. The methyl difluoromethyl ether is chlorinated to produce a reaction mixture including at least one compound of the formula $CF_2HOCH_{3-z}Cl_z$, wherein z is 1, 2, or 3. The mixture can then be fluorinated, or any one of the chlorination compounds first separated from the mixture and separately fluorinated.

However, during the chlorination of $CF_2HOCH_3$, it is difficult to control the distribution of products. Although manipulation of the molar flow rates of $Cl_2$ and $CF_2HOCH_3$ can give a slight predominance of $CF_2HOCH_2Cl$ or $CF_2HOCHCl_2$, a significant amount of $CF_2HOCCl_3$ is formed. If the desired product to be subsequently fluorinated is either $CF_2HOCH_2Cl$ or $CF_2HOCHCl_2$, the formation of $CF_2HOCCl_3$ causes a considerable reduction in the efficiency of the process.

Accordingly, it is an object of the present invention to provide an improved process for the production of bis(difluoromethyl) ether.

It is an further object of the present invention to provide an improved process for the production of bis(difluoromethyl) ether wherein the various required separations may be effected by distillation without loss of yield and danger of explosion due to marked instability of the various intermediates.

It is a still further object of the present invention to provide a process for efficiently producing difluoromethyl methyl ether.

SUMMARY OF THE INVENTION

The problems of the prior art have been overcome by the present invention, which provides a process for the production of difluoromethyl methyl ether. More specifically, the process of the present invention includes means for preferentially inhibiting the formation of $CF_2HOCCl_3$, and which does not produce carcinogens as intermediates.

The unstable complex mixture of chlorinated ethers, some of which are carcinogens, in accordance with the prior art, is avoided in the present invention by employing methyl difluoromethyl ether as a starting material. The methyl difluoromethyl ether is chlorinated to give a chlorinated reaction mixture including at least one compound of the formula $CF_2HOCH_{3-z}Cl_z$, wherein z is 1, 2 or 3, which compound can be readily separated from the chlorinated reaction mixture. The chlorination of methyldifluoromethyl ether would generally form only three derivatives, i.e., z=1, z=2 and z=3. The dichloromethyl difluoromethyl ether (z=2) can be readily separated from the chlorinated reaction mixture and is then fluorinated, with or without such separation, to form the bis(difluoromethyl)ether. The production of $CF_2HOCCl_3$ (z=3) can be inhibited, and any produced also may be separated from the chlorination reaction product and fluorinated. Alternatively, the chlorination reaction product itself may be fluorinated (without prior separation) as follows:

    (I)

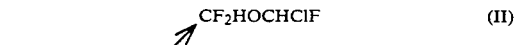    (II)

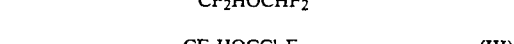

    (III)

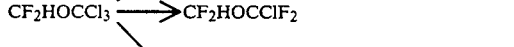

All of the above would find utility as refrigerants, especially (1) monofluoromethyl difluoromethyl ether and (11) bis(difluoromethyl)ether, which are considered to be substitutes for R-11 and R-114 refrigerants, respectively.

DETAILED DESCRIPTION OF THE INVENTION

The methyl difluoromethyl ether which is regarded as the starting material for the process of the present invention is a known compound which may be prepared in the manner reported by Hine and Porter in their aforementioned article published in the Journal of the

*American Chemical Society.* Specifically, difluoromethyl methyl ether is produced by reaction of sodium methoxide (NaOMe) with chlorodifluoromethane (CF$_2$HCl), which reaction may be represented as follows:

$$CF_2HCl + CH_3ONa \rightarrow CF_2HOCH_3 + NaCl$$

Briefly, the method involves forming an alcohol solution of sodium methoxide and bubbling the chlorodifluoromethane slowly into the reaction mixture to obtain the methyldifluoromethyl ether as a residue in the reaction mixture. Some product is entrained with unreacted CF$_2$HCl and can be separated from it in a distillation operation.

The starting ether, CHF$_2$OCH$_3$, also might be prepared by first reacting NAOH with CH$_3$OH, in effect making CH$_3$ONa, and then reacting it with CF$_2$HCl. However, water is also formed in the NaOH/CH$_3$OH reaction. The effect water has on the subsequent reaction to form CHF$_2$OCH$_3$ is to reduce the yield of CHF$_2$OCH$_3$.

The chlorination and fluorination steps of this invention can be represented as follows:

$$CHF_2OCH_3 \xrightarrow{zCl_2} CF_2HOCH_{3-z}Cl_z + zHCl$$

(wherein z = 1, 2, or 3)

$$CF_2HOCH_{3-z}Cl_z \xrightarrow{F} CF_2HOCH_{3-z}Cl_{z-y}F_y$$

(wherein z = 1, 2, or 3
y = 1, 2, or 3
y ≦ z)

The inventors of the present invention have found that the formation of CF$_2$HOCH$_{3-z}$Cl$_z$ wherein z=3 in the above reaction scheme can be inhibited or even eliminated upon the addition of an oxygen source, preferably air, to the vapor phase chlorination reaction medium. Rather than inhibiting the three chlorination products equally, the addition of oxygen surprisingly preferentially inhibits the formation of CF$_2$HOCCl$_3$, Although the inventors of the present invention are not to be limited by any mechanism theory, it is believed that the inhibition is caused as a result of oxygen forming a complex with the activated chlorine molecule, with the kinetics of the reaction being such that the trichloro derivative is preferentially inhibited. Any oxygen source not deleterious to the production of the desired compounds could be used, including oxygen-containing compounds which liberate oxygen in situ.

The oxygen should be present in an amount effective for the desired inhibition. In the case of air, preferably the air is added in an amount from about 1.5 to about 5.5% of the total gas flow. Those skilled in the art will recognize that where pure oxygen is used, the amounts will be about 1/5 that of air. Preferably the oxygen source is added to the reaction medium for as long as the chlorine gas is flowing.

It has been found that CHF$_2$OCH$_3$ may be suitably chlorinated by liquefying the CHF$_2$OCH$_3$ and reacting it with chlorine gas while irradiating with a source of visible light. Alternatively, one may use other light sources such as ultraviolet light or heat, a catalyst or a free radical initiator to aid in the reaction. The chlorination products of CHF$_2$OCH$_3$ can be readily separated prior to fluorination or the reaction mixture can be fluorinated without separation to give an admixture of CF$_2$HOCCl$_2$F, CF$_2$HOCF$_2$Cl, CF$_2$HOCH$_2$F, CF$_2$HOCFHCl, CF$_2$HOCF$_2$H. All separations may be effected by fractional distillation.

A preferred method of chlorinating the CHF$_2$OCH$_3$ is to maintain the CHF$_2$OCH$_3$ in a vapor phase and react it with chlorine gas while subjecting the chlorination reaction to a source of light, preferably visible or ultraviolet light. Alternatively, other reaction aids such as a catalyst, heat or a free radical initiator may be used instead of light in the chlorination reaction.

In the preferred fluorination procedure, the chlorinated reaction product is reacted with anhydrous hydrogen fluoride (HF), which reaction may be represented as follows:

$$2CF_2HOCCl_3 + 3HF \rightarrow CF_2HOCFCl_2 + CF_2HOCF_2Cl + 3HCl$$

Utilizing the above reaction with hydrogen fluoride the inventor has obtained a yield as high as 78% CF$_2$HOCF$_2$Cl With a small amount of CF$_2$HOCFCl$_2$. This was an unexpected result since HF by itself does not normally replace a halogen such as chlorine, except perhaps at very high temperatures, but instead fluorinates by continuous regeneration of a fluorinating agent such as SbCl$_{5-y}$F$_y$, such as SbF$_3$, or SbF$_3$Cl$_2$. Apparently, the difluoromethoxy group activates the chlorine on the alpha-carbon atom, allowing it to react readily with HF.

Alternatively, the HF may be diluted with an organic solvent, preferably a dipolar aprotic solvent such as methyl pyrrolidone, in order to reduce fragmentation of the fluorinated material, resulting in higher yields of desired product with less by-product generation. Other sources of fluorine for the fluorination step include metal fluorides that can form salts of the HF$_2$@ anion, such as KHF$_2$, NaHF$_2$, LiHF$_2$, NH$_4$HF$_2$, etc., and pyridine salts of HF and NaF and KF in suitable solvents.

The resultant fluorinated products may be separated by distillation or by the process as taught in U.S. Pat. No. 4,025,567 or U.S. Pat. No. 3,887,439 which are incorporated herein by reference in their entirety.

The present invention will now be further illustrated by the following examples.

EXAMPLE 1 a) Preparation of CF$_2$HOCH$_3$

A 25 wt % solution of sodium methoxide in reethanol (1533.1 g) containing 7.1 moles of sodium methoxide was placed in a 4 liter jacketed autoclave fitted with a temperature sensor, a pressure gauge and a disleg. The vessel was cooled to 0° to 5° C. and chlorodifluoromethane (318.2 g, 3.70 moles) added over a period of 2.5 hours with agitation. When the addition of gas had been completed, the autoclave was slowly warmed to about 60° C. while venting gaseous products through the water-cooled condenser into a collection trap cooled to about −70° C.

When all volatile material had been collected unreacted CHF$_2$Cl was removed at −20° C. and the remaining CF$_2$HOCH$_3$ transferred to a metal cylinder. The recovered difluoromethyl methyl ether (150.0 g, 1.83 moles) represented a yield of 49.4% based on CF$_2$HCl.

b) Chlorination of CF$_2$HOCH$_3$

Chlorine and CF$_2$HOCH$_3$ in a gaseous phase are passed through separate condensers cooled to 0° C. and then the gas streams combine and pass into one arm of a U-shaped reactor, irradiated with visible light or UV. Both arms of the reactor are jacketed and cooled with water.

There is an outlet at the bottom of the U to which is attached a product collection flask. A Dewar-type condenser cooled to −50° C. is attached to the outlet of the second arm of the U-tube and, in turn, it is connected in series with a cold trap to collect unreacted chlorine and an NAOH scrubber to remove HCl. The reaction is normally carried out at atmospheric pressure, but higher or lower pressure can be used. Temperature should not be allowed to rise much above 50° C. in the reactor to avoid attack on the glass.

In practice, the apparatus is flushed with nitrogen and then chlorine and $CHF_2OCH_3$ are fed to the reactor at rates such that the ratio of the flow of chlorine to that of the ether is maintained at about 2.5:1 for optimum results, i.e., yield of $CF_2HOCHCl_2$. A predominant amount of any one of the three products can be obtained by changing the ratio of the gas flows.

After the passage of 2.3 moles of chlorine and 0.9 moles of $CHF_2OCH_3$, 136.6 g of product were recovered. GC analysis of the product mixture showed $CF_2HOCH_2Cl$ 10.0%, $CF_2HOCHCl_2$ 62.4%, and $CF_2HOCCl_3$ 22.2%.

c) Fluorination of $CHF_2OCHCl_2$ with HF

The chlorinated $CHF_2OCH_3$ (40.0 g) containing 46.1% $CF_2HOCHCl_2$ in a stainless steel cylinder was then cooled in ice before adding anhydrous HF (30.0 g). The cylinder was closed with a valve and pressure gauge and then was placed in a water bath at 60° C. for 3 hours. The cylinder was then vented through a NAOH scrubber and volatile products collected in a trap cooled at −70° C. The weight of product recovered from the trap was 16.8 g. It contained 71.8% $CF_2HOCF_2H$ by GC analysis, corresponding to a yield of 83.8% of $CF_2HOCF_2H$.

When conducted on a larger scale (e.g., 5 gallons), almost quantitative yields of $CF_2HOCF_2H$ (based on $CF_2HOCHCl_2$) were obtained.

EXAMPLE 2

A sample of chlorinated difluoromethyl ether mixture (25 g) containing 50% $CF_2HOCCl_3$, was placed in a polyethylene flask fitted with an inlet tube for nitrogen as carrier gas, an outlet tube leading to a second polyethylene flask containing NAOH solution (10%), followed by a drying tube and a trap cooled in Dry Ice/MeOH.

An excess of anhydrous hydrogen fluoride was added to the chlorinated ether and the mixture stirred with a magnetic stirrer. Heat was not applied, the temperature remaining at about 20° C. More hydrogen fluoride was added to the mixture as needed until all the organic material had reacted. The weight of material collected from the cold trap was 9.5 g.

Analysis of the recovered product by GC showed it to consist of 84.3% $CF_2HOCF_2Cl$, a yield of 78% based on the $CF_2OCCl_3$ content of the chlorinated mixture. A small amount of $CF_2HOCFCl_2$ was also present.

EXAMPLE 3

The chlorination apparatus consisted of two vertical lengths of jacketed glass tubing, 4 feet long by 2 inches I.D., connected at the lower ends in a U-tube fashion by a short length of unjacketed 2 inch I.D. tubing. A drain tube led from the lowest point of the U-tube arrangement so that product could be collected as it formed and removed continuously from the apparatus or alternatively allowed to accumulate in a receiver. Three 150 watt incandescent flood lamps were arranged along the length of each tube.

The gases were fed into the upper end of one arm of the U-tube arrangement. Flow rates were measured by calibrated mass flowmeters. A low temperature condenser on the outlet of the second arm of the U-tube returned unreacted E-152a and chlorine to the illuminated reaction zone. Hydrogen chloride by-product and air passed through the condenser into a water scrubber where the hydrogen chloride was removed.

A mixture of methanol and water, cooled to 0° to 5° C. was circulated through the cooling jackets of the apparatus.

In a typical run, coolant at a temperature of 0° to 5° C. is circulated through the cooling jackets, the flood lamps were turned on and dry ice placed in the low temperature condenser. Chlorine was introduced into the apparatus first, followed by difluoromethyl ether and air in the desired ratios. Product was removed at intervals from the receiver and washed with saturated $NaHCO_3$ solution to remove HCl. Since the reaction was continuous, it could proceed for any length of time desired. At the end of the reaction, gas flows were stopped and product allowed to drain from the vertical reactor tubes into the receiver.

The results are tabulated irk Table I below. Examples 6-29-1 to 6-29-7 show the distribution of products normally obtained without the addition of air to the gas stream. Examples 7-7-3 through 7-8-6 show the effect of the addition of air in diminishing amounts, in accordance with the present invention.

TABLE 1

| Run No. | Flow Rates (mls/min) | | | Product Weight (gms) | Product Distribution | | | Moles | | Mole Ratio $Cl_2$/E-152a | Air in Total Gas Flow (%) | Air in Chlorine (%) |
|---|---|---|---|---|---|---|---|---|---|---|---|---|
| | $Cl_2$ | E-152a | Air | | Mono (%) | Di- (%) | Tri- (%) | $Cl_2$ | E152a | | | |
| 6-29-1 | 500 | 273 | — | 69.6 | 6.0 | 42.5 | 33.6 | 0.0203 | 0.0111 | 1.83 | — | — |
| 6-29-2 | 500 | 280 | — | 95.6 | 8.2 | 42.5 | 30.4 | 0.0203 | 0.0114 | 1.78 | — | — |
| 6-29-6 | 510 | 270 | — | 81.4 | 22.5 | 38.5 | 33.7 | 0.0207 | 0.0110 | 1.88 | — | — |
| 6-29-7 | 500 | 280 | — | 79.1 | 23.2 | 42.3 | 37.2 | 0.0203 | 0.0114 | 1.78 | — | — |
| 7-7-3 | 870 | 380 | 67 | 69.3 | 55.0 | 32.9 | 2.8 | 0.0353 | 0.0154 | 2.29 | 5.4 | 7.7 |
| 7-7-4 | 850 | 440 | 65 | 96.8 | 56.8 | 37.0 | 3.5 | 0.0345 | 0.0179 | 1.93 | 5.1 | 7.6 |
| 7-7-5 | 900 | 405 | 63 | 119.3 | 48.3 | 42.4 | 5.2 | 0.0365 | 0.0164 | 2.23 | 4.8 | 7.0 |
| 7-7-7 | 900 | 405 | 60 | 116.0 | 54.3 | 39.8 | 4.5 | 0.0365 | 0.0164 | 2.23 | 4.6 | 6.7 |
| 7-7-8 | 930 | 405 | 62 | 111.5 | 52.5 | 36.2 | 3.3 | 0.0378 | 0.0164 | 2.30 | 4.6 | 6.7 |
| 7-8-2 | 1430 | 600 | 55 | 198.5 | 43.0 | 45.2 | 7.2 | 0.0581 | 0.0244 | 2.38 | 2.7 | 3.8 |
| 7-8-3 | 1850 | 750 | 54 | 202.4 | 42.8 | 46.5 | 5.0 | 0.0751 | 0.0305 | 2.46 | 2.1 | 2.9 |
| 7-8-6 | 2200 | 1030 | 51 | 213.0 | 33.6 | 56.9 | 7.7 | 0.0893 | 0.0418 | 2.14 | 1.6 | 2.3 |

What is claimed is:

1. A process for the preparation of fluorinated dimethyl ethers of the formula $CF_2HOCCl_xF_yH_{3-(x+y)}$, wherein x is 0, 1 or 2 and y is 1, 2 or 3 and wherein the total of x+y is 1, 2, or 3, said process comprising:

chlorinating $CHF_2OCH_3$ by reacting said $CHF_2OCH_3$ with chlorine in the presence of oxygen to form a chlorinated admixture containing at least one compound of the formula $CF_2HOCH_{3-z}Cl_z$, wherein z is 1 or 2, and inhibiting the formation of $CF_2HOCCl_3$; and fluorinating said at least one compound of the formula $CF_2HOCH_{3-z}Cl_z$ with a fluorine source selected from the group consisting of hydrogen fluoride, anhydrous hydrogen fluoride, metal salts of $HF_2^\ominus$, NaF, KF and pyridine salts of HF, in the absence of a catalyst to obtain a fluorinated admixture containing at least one compound of formula $CF_2HOCH_{3-z}F_yCl_{z-y}$.

2. A process in accordance with claim 1 wherein said chlorination step occurs in either a vapor or liquid phase and the chlorine is in the form of a liquid or a gas.

3. A process in accordance with claim 1 wherein said chlorination step is in the vapor phase and the chlorine is in the form of a gas.

4. A process in accordance with claim 1 wherein the fluorine source is selected from the group consisting of anhydrous hydrogen fluoride and hydrogen fluoride in an organic solvent.

5. A process in accordance with claim 1 wherein said at least one compound of the formula $CF_2HOCH_{3-z}Cl_z$ is $CF_2HOCHCl_2$ and said fluorinated reaction product includes $CF_2HOCF_2H$ and $CF_2HOCHFCl$.

6. A process in accordance with claim 1 wherein said at least one compound of the formula $CF_2HOCH_{3-z}Cl_z$ is $CF_2HOCHCl_2$ and said at least one compound of the formula $CF_2HOCCl_xF_yH_{3-(x+y)}$ is $CF_2HOCF_2H$, and further comprising separating and recovering said $CF_2HOCF_2H$ from said fluorinated admixture.

7. A process in accordance to claim 1 wherein said chlorination is conducted at a temperature and pressure sufficient to maintain said $CF_2HOCH_3$ in a gaseous state.

8. A process in accordance with claim 1 further comprising reacting $CHF_2Cl$ with an alkali metal methoxide in solvent solution to form said $CHF_2OCH_3$.

9. A process in accordance with claim 1, wherein air is the source of said oxygen.

10. In a process for the preparation of fluorinated dimethyl ethers of the formula $CF_2HOCCl_xF_yH_{3-(x+y)}$, wherein x is 0, 1 or 2 and y is 1, 2 or 3 and wherein the total of x+y is 1, 2, or 3, wherein $CHF_2OCH_3$ is chlorinated by reacting said $CHF_2OCH_3$ with chlorine to form a chlorinated admixture containing at least one compound of the formula $CF_2HOCH_{3-z}Cl_z$, wherein z is 1 or 2, and said at least one compound of the formula $CF_2HOCH_{3-z}Cl_z$ is fluorinated with a fluorine source selected from the group consisting of hydrogen fluoride, anhydrous hydrogen fluoride, metal salts of $HF_2$, NaF, KF and pyridine salts of HF, in the absence of a catalyst to obtain a fluorinated admixture containing at least one compound of formula $CF_2HOCH_{3-z}F_yCl_{z-y}$, the improvement comprising inhibiting the formation of $CF_2HOCH_{3-z}Cl_1$ wherein z is 3 by conducting said chlorination step in the presence of oxygen.

11. The process of claim 10 wherein air is the source of said oxygen.

* * * * *